United States Patent [19]

Giede et al.

[11] 4,275,235
[45] Jun. 23, 1981

[54] PREPARATION OF QUATERNARY AMMONIUM HALIDES IN POWDER OR GRANULAR FORM

[75] Inventors: Wolfgang Giede, Hilden; Horst Rutzen, Langenfeld, both of Fed. Rep. of Germany

[73] Assignee: Henkel Kommanditgesellschaft auf Aktien, Düsseldorf-Holthausen, Fed. Rep. of Germany

[21] Appl. No.: 94,961

[22] Filed: Nov. 16, 1979

[30] Foreign Application Priority Data

Dec. 9, 1978 [DE] Fed. Rep. of Germany ....... 2853241

[51] Int. Cl.$^3$ .............................................. C07C 85/04
[52] U.S. Cl. .................................................. 564/288
[58] Field of Search ................. 260/567.6 M, 567.6 R

[56] References Cited

U.S. PATENT DOCUMENTS

| 2,075,958 | 4/1937 | Piggott | 260/567.6 M |
| 2,087,132 | 7/1937 | Taub et al. | 260/567.6 M |
| 2,395,989 | 3/1946 | Bock et al. | 260/567.6 M |
| 2,687,414 | 8/1954 | Cusic | 260/567.6 M |
| 3,497,556 | 2/1970 | Lanner et al. | 260/567.6 M |

Primary Examiner—Natalie Trousof
Assistant Examiner—James H. Reames
Attorney, Agent, or Firm—Hammond & Littell, Weissenberger and Muserlian

[57] ABSTRACT

Quaternary ammonium halides in powder or granular form are prepared by reacting tertiary amines and excess alkyl halides in the absence of solvent at elevated temperature and pressure and conducting the hot, pressurized reaction mixture into an area under lower pressure where the excess alkyl halides vaporize and the quaternary ammonium halides are recovered in powder or granular form.

9 Claims, No Drawings

PREPARATION OF QUATERNARY AMMONIUM HALIDES IN POWDER OR GRANULAR FORM

FIELD OF THE INVENTION

This invention is directed to the preparation of quaternary ammonium halides. More specifically, this invention is directed to a process for the preparation of quaternary ammonium halides in powder or granular form.

BACKGROUND OF THE INVENTION

Quaternary ammonium halides can be prepared according to known methods by reacting tertiary amines with alkyl halides. This reaction is generally carried out in polar solvents, preferably in water, ethanol, isopropanol, or a mixture thereof. It is necessary to use considerable quantities of solvents, especially in the preparation of quaternary ammonium halides having longer chain alkyl radicals, since these compounds have only a limited solubility and their concentrated solutions have the undesirable property of forming a gel. The upper concentration limit of quaternary ammonium halides in solution is thus, in practice, about 50% by weight; however, in many cases, it is necessary to work with concentrations of 20% by weight or less.

If large quantities of solvent are used, the capacity of the reaction vessels is not fully utilized. Also, if the quaternary ammonium halides thus produced are recovered from the solvent by evaporation, then additional energy has been expended. Further, when the products are used in the form which they are obtained, namely, as solutions, additional expenditures for transportation are oftentimes required.

It has been surprisingly discovered that quaternary ammonium halides can be obtained in a simple manner, free from solvents, and in finely-divided form.

OBJECTS OF THE INVENTION

It is an object of this invention to provide a process to prepare quaternary ammonium halides.

It is also an object of this invention to provide a process of preparing quaternary ammonium halides in powder or granular form.

It is further an object of this invention to provide a process for preparation of quaternary ammonium halides in the absence of solvent.

These and other objects of the invention will become more apparent in the discussion below.

DETAILED DESCRIPTION OF THE INVENTION

This invention is directed to a process for the preparation of quaternary ammonium halides in the form of powder or granules by reacting tertiary amines with alkyl halides at elevated temperature and elevated pressure. The process is characterized in that tertiary amines are reacted with an alkyl halide in the absence of solvents, and that the reaction mixture, which is under elevated pressure, is subsequently conducted into a tank or other area which is maintained under a lower pressure and which is where the excess alkyl halide vaporizes and the quaternary ammonium halides separate in the form of powder or granules.

According to the process of the invention, the alkyl halides are lower alkyl halides having from 1 to 4 carbon atoms. Preferably the alkyl halide is selected from the group consisting of methyl chloride, methyl bromide, methyl iodide, ethyl chloride, and ethyl bromide.

The process is particularly suitable for the quaternization of tertiary amines which contain, in addition to two alkyl or hydroxyalkyl radicals with from 1 to 3 carbon atoms, a longer-chained alkyl or $\beta$-hydroxy-alkyl radical with from 8 to 18 carbon atoms. Examples of suitable tertiary amines with a longer-chained alkyl radical include the following: dimethyl-octylamine, dimethyl-decylamine, diethyl-decylamine, dimethyl-dodecylamine, di-n-propyl-dodecylamine, diethyl-tetradecylamine, dimethyl-hexadecylamine, di-n-propyl-hexadecylamine, dimethyl-octadecylamine, bis-(2-hydroxyethyl)-decylamine, bis-(2-hydroxypropyl)-dodecylamine, bis-(2-hydroxyethyl)-hexadecylamine, and bis-(2-hydroxyethl)-octadecylamine.

Also suitable as starting materials for the preparation of quaternary ammonium halides according to the invention are tertiary amines or mixtures of tertiary amines with a longer-chained $\beta$-hydroxyalkyl radical. These can be obtained according to known methods from longer-chained epoxy-alkanes or epoxy-alkane mixtures with 8 to 18 carbon atoms and terminal or non-terminal, i.e., interior, epoxy groupings, by reaction with dialkylamines, such as dimethylamine, diethylamine, and di-n-proplyamine, as well as by reaction with dihydroxyalkylamines, such as diethanolamine and dipropanolamine. For the preparation of these tertiary amines, mixtures of epoxy-alkanes of varying chain length are primarily used as starting materials. Among the epoxyalkanes with interior epoxy groups, the preferred compounds are mixtures of compounds where the epoxy groupings are distributed at random over the inner positions existing in the hydrocarbon chain. Examples of such tertiary amines include the following: dimethyl-2-hydroxydecylamine, bis-(2-hydroxyethyl)-2-hydroxydecylamine, diethyl-2-hydroxydodecylamine, bis-(2-hydroxyethyl)-2-hydroxydodecylamine, the reaction product of dimethylamine with a 1,2-epoxy-alkane mixture of the chain length $C_{12-14}$, the reaction product of diethylamine with a 1,2-epoxy-alkane mixture of the chain length $C_{14-16}$, the reaction product of di-n-propylamine with a 1,2-epoxy-alkane mixture of the chain length $C_{16-18}$, the reaction product of diethanolamine with a 1,2-epoxy-alkane mixture of the chain length $C_{14-16}$, the reaction product of dimethylamine with an epoxy-alkane mixture of the chain length $C_{11-14}$ with interior epoxy groupings in random distribution, the reaction product of diethylamine with an epoxy-alkane mixture of the chain length $C_{14-16}$ with interior epoxy groupings in random distribution, the reaction product of di-n-propylamine with an epoxy-alkane mixture of the chain length $C_{15-18}$ with interior epoxy groupings in random distribution, and the reaction product of diethanolamine with an epoxy-alkane mixture of the chain length $C_{11-14}$ with interior epoxy groupings in random distribution.

The alkyl halide used as a quaternizing agent is always used in excess, according to the process of the invention. Preferably, the reaction is carried out at a molar ratio of tertiary amine to alkyl halide of from about 1:3 to 1:8, most preferably at a molar ratio of from about 1:5 to 1:6.

The reaction between tertiary amine and alkyl halide is carried out under the pressure and temperature conditions customary for these quaternization reactions, such as pressure of from about 5 to 25 bar and temperature of from about 60° to 100° C. In many cases the autogenous pressure established over the reaction mixture is sufficient for a satisfactory course of the reaction. If necessary, the pressure can be increased by introducing inert gases, such as nitrogen, carbon dioxide, methane, ethane, propane or butane, or a mixture thereof.

Reaction vessels normally useful for carrying out the process of the invention include pressure reactors which are equipped with a heating and cooling unit, a stirring mechanism, and a suitable valve for discharging the reaction product under pressure.

The mixture resulting from the quaternization reaction is preferably conducted immediately after the reaction, without substantial cooling and/or pressure reduction in the reactor, out the above-mentioned valve and, if necessary, through a suitable nozzle such as an expansion nozzle, into a vessel or separate area which is under a lower pressure than the reactor, preferably under normal, i.e., atmospheric, pressure. The excess alkyl halide in the reaction mixture expands to a gaseous state immediately, while the quaternary ammonium halide is obtained in finely divided, solid form. The expanded alkyl halide can be condensed by means of a compressor or a suitable cooling arrangement and can be used again. Naturally, quaternary ammonium halides which have already been formed by other processes can also be treated this way to form powders or granules.

The process according to the invention for the preparation of quaternary ammonium halides can also be carried out continuously. The reaction components can be pumped into a suitable heated pressure reaction pipe of suitable length and then into a suitable series of vessels. At the end of the reactor unit, an expansion valve is arranged which is set to the given reaction pressure. The reaction mixture is then conducted into a tangential separator. The quaternary ammonium halide accumulates in the bottom part of the separator, while the gaseous alkyl halide is exhausted from the top of the separator and fed to a compressor or brine cooler.

The following examples are intended to illustrate the invention and are not to be construed as limiting the invention thereto.

EXAMPLES

Example 1

Two hundred and twenty-five grams (1 mol) of $C_{8-18}$-alkyl-dimethylamine [dimethyl-cocoalkylamine; amine number 249] and 303 g (6 mols) of methyl chloride were heated under stirring in a one-liter autoclave having a stirrer and bottom valve, until the exothermic reaction was initiated at 70° C. The temperature rose rapidly to 77° and then dropped off. The stirring was continued at 70° C. Thirty minutes after the temperature of the mixture attained 70° C., the amine number dropped to 1.1, as was determined by analysis of a sample taken from the bottom valve. The autoclave pressure reached 15 bar. The $C_{8-18}$-alkyl-trimethyl ammonium chloride was recovered by discharging the reaction mixture containing excess methyl chloride and at a temperature of 70° C. and a pressure of 15 bar, through the bottom valve into a one-liter powder bottle where it separated as a granular, white product which dissolved clear in water.

Example 2

An amount of 266 g (1 mol) of dimethyl-hexadecylamine [amine number 211] and 303 g (6 mols) of methyl chloride were heated in a one-liter autoclave under stirring to 70° C. The pressure rose to 14 bar, and an exothermic heat effect was observed. After 35 minutes the reaction was complete, and the amine number dropped to 3.2. The hexadecyl-trimethyl-ammonium chloride product obtained at 70° C. under a pressure of 14 bar was recovered by conducting the reaction mixture directly into a powder bottle where it separated as a pure white, fine powder. The product dissolved clear in water and foamed considerably.

Example 3

An amount of 239 g (0.9 mol) of dimethyl-hexadecylamine [amine number 211] and 271 g (4.2 mols) of ethyl bromide were heated in a one-liter autoclave under stirring to 100° C., and the pressure rose to 13 bar. The reaction mixture was stirred for ten hours at this temperature. The resulting hexadecyl-trimethyl-ammonium bromide mixture was then passed directly into a powder bottle without cooling and separated as granules which dissolved clear in water. The product was not hygroscopic. According to an analysis, the product consisted of 95% quaternary ammonium halide.

Example 4

Dimethyl-2-hydroxy-$C_{12-14}$-alkylamine [amine number 218], which had been obtained by reacting dimethylamine with a mixture of 1,2-epoxy-alkanes of the chain length $C_{12-14'}$ was used as starting material. Nitrogen was introduced to a mixture of 386 g (1.5 mols) of this tertiary amine and 445 g (9 mols) of methyl chloride in a one-liter, stirrer equipped autoclave, up to a pressure of 10 bar. Subsequently the product was heated to 80° C. and the pressure rose to 21 bar. The reaction mixture was kept at this temperature for five hours. The 2-hydroxy-$C_{12-14}$-alkyl-trimethylammonium chloride obtained in this reaction was expanded at 75° C. into a powder bottle, and a white hygroscopic powder with an amine number of 2 was precipitated, which powder dissolved clear in water.

Example 5

Dimethyl-2-hydroxy-$C_{16-18}$-alkylamine [amine number 180], which had been obtained by reacting dimethylamine with a mixture of 1,2-epoxy-alkanes of the chain length $C_{16-18'}$ was used as starting material. Nitrogen was introduced to a mixture of 468 g (1.5 mols) of this tertiary amine and 455 g (9 mols) of methyl chloride in a one-liter, stirrer equipped autoclave, up to a pressure of 10 bar. Then, the contents of the autoclave were heated to 80° C. and kept at that temperature for five hours. The reaction mixture, which contained 2-hydroxy-$C_{16-18}$-alkyl-trimethyl-ammonium chloride and was at 80° C. under a pressure of 21 bar, was expanded through the bottom valve into a powder bottle. The product separated as a white hygroscopic powder with an amine number of 1.4.

Example 6

Dimethyl-$\beta$-hydroxy-$C_{11-14}$-alkylamine [amine number 225], which had been obtained from a mixture of $C_{11-14}$-epoxy alkanes with interior epoxy groupings in random distribution by reaction with dimethylamine, was used as starting material. Five hundred grams (2 mols) of this amine and 606 g (12 mols) of methyl chloride were heated, as in Example 5, under a nitrogen pressure of 10 bar to 80° C. and kept at that temperature for five hours until a pressure of 18 bar was established.

In the expansion of the reaction mixture at 80° C. through the bottom valve, β-hydroxy-$C_{11-14}$-alkyl-trimethyl-ammonium chloride was separated as a hygroscopic white powder. The product had an amine number of 1.8 and dissolved clear in water.

Example 7

A starting material comprising dimethyl-β-hydroxy-$C_{15-18}$-alkylamine [amine number 179], which had been obtained from a mixture of $C_{15-18}$-epoxy alkanes with interior epoxy groupings in random distribution by reaction with dimethyl amine, was used. Four hundred seventy grams (1.5 mols) of this tertiary amine and 455 g (9 mols) of methyl chloride were heated as in Example 5, under a nitrogen pressure of 10 bar to 80° C. and kept at that temperature for five hours, with the pressure rising to 21 bar. By expansion of the reaction mixture at 80° C. through the bottom valve, β-hydroxy-$C_{15-18}$-alkyl-trimethyl-ammonium chloride separated as a yellowish powder with an amine number of 18.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of quaternary ammonium halide in the form of powder or granules, which comprises reacting tertiary amine containing two alkyl or hydroxyalkyl radicals with from 1 to 3 carbon atoms and an alkyl radical or β-hydroxyalkyl radical with from 8 to 18 carbon atoms, with excess alkyl halide, the alkyl halide being selected from the group consisting of methyl chloride, methyl bromide, methyl iodide, ethyl chloride, and ethyl bromide, in the absence of solvent at elevated temperature and elevated pressure and conducting the hot reaction mixture, which is under elevated pressure, into an area which is under a lower pressure, where excess alkyl halide vaporizes under the elevated temperature conditions, separating the quaternary ammonium halide in the form of powder or granules.

2. The process of claim 1 wherein the molar ratio of tertiary amine to alkyl halide is from about 1:3 to 1:8.

3. The process of claim 1 wherein the tertiary amine and alkyl halide are reacted at a pressure of from about 5 to 25 bar.

4. The process of claim 1 wherein the tertiary amine and alkyl halide are reacted at a temperature of from about 60° to 100° C.

5. The process of claim 1 wherein the hot reaction mixture is conducted into an area under atmospheric pressure.

6. A process of claim 1 for the preparation of quaternary ammonium halide in the form of powder or granules, which comprises reacting tertiary amine containing two alkyl or hydroxyalkyl radicals with from 1 to 3 carbon atoms and an alkyl radical or β-hydroxyalkyl radical with from 8 to 18 carbon atoms, with excess alkyl halide, the alkyl halide being selected from the group consisting of methyl chloride, methyl bromide, methyl iodide, ethyl chloride, and ethyl bromide, in the absence of solvent at elevated temperature and elevated pressure and conducting the hot reaction mixture, which is under elevated pressure, through a valve suitable for discharging the reaction product under pressure into an area which is under a lower pressure, where excess alkyl halide vaporizes under the elevated temperature conditions, separating the quaternary ammonium halide in the form of powder or granules.

7. The process of claim 6 wherein the hot reaction mixture is conducted through an expansion valve wherein the excess alkyl halide expands to a gaseous state.

8. The process of claim 1 wherein the hot, pressurized mixture is discharged into an area which is maintained under normal pressure.

9. The process of claim 1 wherein the hot, pressurized reaction mixture is depressurized through an expansion valve.

* * * * *